United States Patent [19]

Salzburg et al.

[11] Patent Number: 4,667,041

[45] Date of Patent: May 19, 1987

[54] PROCESS FOR THE PREPARATION OF 3-HYDRAZINO-1,2-BENZ-ISOTHIAZOLE 1,1-DIOXIDES

[75] Inventors: Herbert Salzburg; Manfred Hajek, both of Cologne; Gerd Hänssler, Leverkusen, all of Fed. Rep. of Germany

[73] Assignee: Bayer Aktiengesellschaft, Leverkusen, Fed. Rep. of Germany

[21] Appl. No.: 706,577

[22] Filed: Feb. 28, 1985

[30] Foreign Application Priority Data

Mar. 8, 1984 [DE] Fed. Rep. of Germany ....... 3408539

[51] Int. Cl.[4] .......................................... C07D 275/06
[52] U.S. Cl. .................................. 548/212; 548/210; 548/207
[58] Field of Search ............... 548/212, 209, 213, 207, 548/210, 472; 514/373

[56] References Cited

U.S. PATENT DOCUMENTS

| | | | |
|---|---|---|---|
| 3,755,512 | 8/1973 | Bayer et al. | 548/213 |
| 4,140,693 | 2/1979 | Wade et al. | 544/369 |
| 4,174,442 | 11/1979 | Wade et al. | 544/256 |
| 4,178,451 | 12/1979 | Wade et al. | 544/333 |

FOREIGN PATENT DOCUMENTS

| | | |
|---|---|---|
| 1670612 | 2/1971 | Fed. Rep. of Germany . |
| 2340815 | 2/1975 | Fed. Rep. of Germany ...... 548/213 |
| 2617807 | 3/1977 | Fed. Rep. of Germany ...... 548/212 |

OTHER PUBLICATIONS

H. Bohme et al., Zeitschrift fur Analytische Chemie 139, 255 et seq. (1953).
E. Schrader, Prakt. Chemie 95, 312–326 (1917).
Bakre, et al., "Reaction of Hydrazine Hydrate on Some Counarins", Indian J. Chem. 20B, pp. 614–615 (1981).
Sharma, et al., Reactions of Hydrazine Hydrate with Phenacyl Bromide," Indian J. Chem. 9, pp. 794–795 (1971).

Primary Examiner—Mark L. Berch
Assistant Examiner—G. Hendricks
Attorney, Agent, or Firm—Sprung Horn Kramer & Woods

[57] ABSTRACT

A process for the preparation of a 3-hydrazino-1, 2-benzisothiazole 1,1-dioxide of the formula

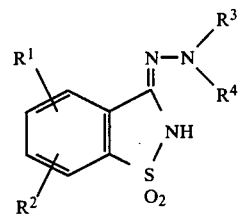

in which
$R^1$ and $R^2$ each independently is hydrogen, alkyl, halogen, amino, hydroxyl or carboxyl, and
$R^3$ and $R^4$ each independently is hydrogen, alkyl, cycloalkyl or aryl, comprising reacting a 3-keto-2H,3H-1,2-benzisothiazole 1,1-dioxide of the formula

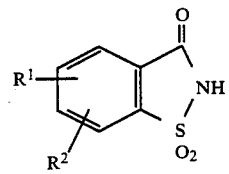

with a hydrazine of the formula

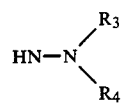

in a molar ratio of 1:1 to 1:50, in an inert solvent, at a temperature between 75° C. and 200° C. and for a reaction time of 15 to 40 hours. The products, some of which are known, are fungicidally active and can also be used as intermediates.

6 Claims, No Drawings

PROCESS FOR THE PREPARATION OF 3-HYDRAZINO-1,2-BENZ-ISOTHIAZOLE 1,1-DIOXIDES

The invention relates to a new process for the preparation of known 3-hydrazino-1,2-benzisothiazole 1,1-dioxides, which, for example, have a pharmacological action or an action in the field of plant protection and can also be used as intermediate products for the synthesis of active compounds for combating pests, in particular as fungicides, in pharmacology, or as polymer activators.

It is already known that 3-hydrazino-1,2-benzisothiazole 1,1-dioxides are obtained when the corresponding 3-chloro or 3-alkoxy derivatives are reacted with hydrazine or substituted hydrazines [see E. Schrader, Prakt. Chemie 95, 312–326 (1917), and U.S. Pat. No. 4,178,451].

Another route to the desired 3-hydrazino compound is via the 3-mercapto compound, which in turn is prepared from the 3-chloro compound.

The 3-chloro compounds are obtained by chlorination of 3-keto-3H,2H-1,2-benzisothiazole 1,1-dioxide with chlorinating agents, such as, for example, phosphorus pentachloride, substantial formation of by-products taking place [see H. Böhme et al., Zeitschrift für Analytische Chemie 139, 255 et seq. (1953)].

All these processes have the common feature that the 3-keto-2H,3H-1,2-benzisothiazole 1,1-dioxides are first converted to intermediate products which carry a chloro, alkoxy or mercapto group in the 3-position, and these are then reacted with optionally substituted hydrazines.

It is also known that 3-hydroxy-1,2-benzisothiazole 1,1-dioxides can be reacted with hydrazine under atmospheric pressure, ring opening taking place to give the o-sulphamidobenzhydrazide [see E. Schrader, Prakt. Chemie 95, 312–326 (1917)]. If the reaction is carried out using an excess of anhydrous hydrazine at 125° C. in a bomb tube, two compounds are obtained. Firstly, 1-amino-2,5-(2-sulphamidophenyl)-1,3,4-triazole, which is formed by elimination of 2 mols of water from the product of the ring-opening reaction—o-sulphamidobenzhydrazine —is obtained, and secondly, the desired 3-hydrazino compound can be obtained in low yields after acidification of the filtrate.

It has now been found that the 3-hydrazino-1,2-benzisothiazole 1,1-dioxides of the formula (I)

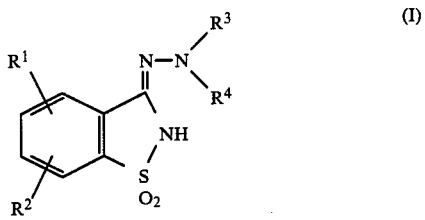

in which
R¹ and R² can be identical or different and represent hydrogen, alkyl, halogen, amino, hydroxyl or carboxyl, and
R³ and R⁴ can be identical or different and rep- represent hydrogen, alkyl, cycloalkyl or aryl, are obtained in very good yields and high purity when 3-keto-2H,3H-1,2-benzisothiazole 1,1-dioxides of the formula (II)

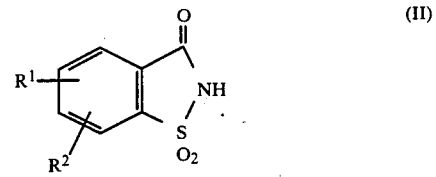

in which R¹ and R² have the meanings given above, are reacted with hydrazines of the formula (III)

in which R³ and R⁴ have the meaning given above, in a molar ratio of at least 1:1 to 1:50, in an inert solvent, at temperatures between 75° C. and 200° C. and for reaction time of 15 to 40 hours.

The compounds of the formula (I) are in general in equilibrium with the compounds of the formula (IA):

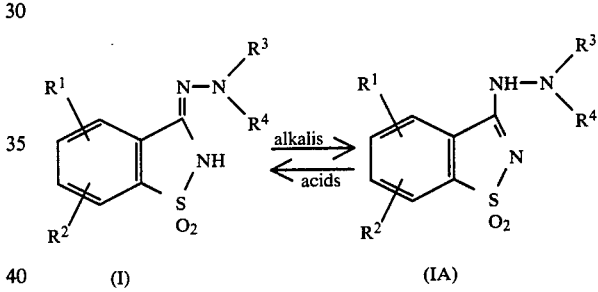

For the sake of simplicity, reference will always be made below to compounds of the formula (I), although the pure compounds or their mixtures with various amounts of the compounds of the formula (I) and (IA) are meant.

It is to be regarded as extremely surprisingly that the reaction, according to the invention, of 3-keto-2H,3H-1,2-benzisothiazole 1,1-dioxides of the formula (II) with hydrazines of the formula (III) gives the desired compounds in such high yield and purity, since, in view of the prior art, it was to be expected that the reaction would take place with ring opening, and mixtures of a very large variety of compounds would be formed.

The process according to the invention has a number of advantages. Thus, the 3-hydrazino compounds of the formula (I) are obtained in a single-stage process, in high yields and high purity. The required starting materials are commercially available or can be readily obtained in good yields by known processes.

If 6-chloro-3-keto-2H,3H-1,2-benzisothiazole 1,1-dioxide and hydrazine hydrate are used as starting materials, the course of the reaction can be represented by the following equation:

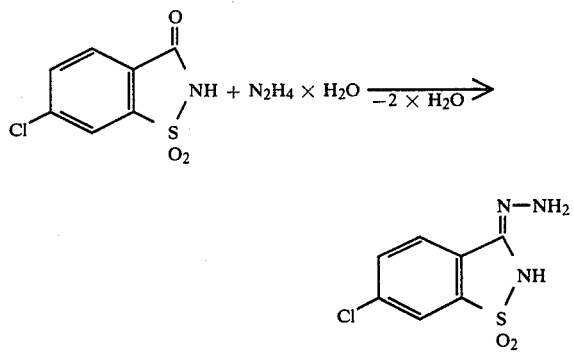

Formula (II) gives a general definition of the 3-keto-2H,3H-1,2-benzisothiazole 1,1-dioxides to be employed as starting compounds. In this formula, $R^1$ and $R^2$ are identical or different and represent hydrogen, alkyl having 1 to 5 carbon atoms, fluorine, chlorine, bromine, amino, hydroxyl or carboxyl.

The 3-keto-2H,3H-1,2-benzisothiazole 1,1-dioxides which can be used according to the invention are already known and can be prepared by well known processes. For example, the following may be mentioned as examples: 3-keto-2H,3H-1,2-benzisothiazole 1,1-dioxide and 5-chloro-, 5-bromo-, 5-methyl-, 5-ethyl- , 5,6-dichloro-, 6-chloro-, 6-bromo-, 6-methyl-, 6-ethyl-, 5-amino-, 5-hydroxy- or 5-carboxy-3-keto-2H,3H-1,2-benzisothiazole 1,1-dioxide.

Formula (III) gives a general definition of the hydrazine furthermore to be employed as a starting compound, or its substitution products.

$R^3$ and $R^4$ are identical or different and represent hydrogen, alkyl having 1 to 6 carbon atoms, such as methyl, ethyl, n- and iso-propyl, n-, sec.-, tert.- and isobutyl, n-pentyl, tert.-pentyl and hexyl, cycloalkyl having 3 to 6 carbon atoms, such as cyclopropyl, cyclopentyl and cyclohexyl, or phenyl.

The compounds which can be used according to the invention, of the formula (III), are known compounds and can be prepared by well known processes. For example, the following may be mentioned as examples: hydrazine, methylhydrazine, ethylhydrazine, n-propylhydrazine, isopropylhydrazine, tert.-butylhydrazine, n-hexylhydrazine, N,N-dimethylhydrazine, N,N-diethylhydrazine, cyclopropylhydrazine, cyclohexylhydrazine and phenylhydrazine.

Suitable solvents for the process according to the invention are all inert organic solvents. These include alcohols, such as, for example, ethanol, propanol, butanols, pentanols and cyclohexyl alcohol, in particular n- and sec.-butanol and pentanol, and aromatic hydrocarbons, such as chlorobenzene, dichlorobenzene and chlorinated xylenes; and furthermore carboxylic acids, such as acetic acid and propionic acid. Mixtures of these solvents can also be used.

The reaction according to the invention is carried out at temperatures between 75° C. and 200° C., preferably between 130° C. and 165° C.

The reaction is carried out under atmospheric pressure.

In carrying out the process according to the invention, the starting compounds ae employed in a molar ratio of at least 1:1, up to a 50-fold excess of the hydrazine component. Preferably, the hydrazine component is employed in a 5- to 10-fold excess, preferably a 7-fold excess.

In the reaction according to the invention, the reaction time is 15 to 40 hours, preferably 30 to 35 hours.

The compounds which can be prepared by the process according to the invention are known, as are their actions, for example pharmacology [(see Whitehead et al., J. Med. Chem. 10, 844 (1967)]. However, they can also be used as intermediate products, for example for the preparation of plant protection agents, polymer activators and pharmaceuticals.

Thus, the compounds of the formula (I), in which $R^3$ and $R^4$ represent hydrogen, can be reacted with aldehydes or ketones under customary conditions, for example to give hydrazones (see Organikum, VEB Deutscher Verlag der Wissenschaften, Berlin 1977). These compounds have pharmacological properties [see Whitehead et al., J. Med. Chem. 10, 844 (1967)]. The action of these secondary products in the field of plant protection is new and forms the subject of an application which has not yet been published; the use of the compounds to be prepared by the process according to the invention in the field of plant protection is also new, not just the use of the reaction products.

The compounds prepared by the process according to the invention, and their secondary products, exhibit a powerful microbicidal action and can be employed in practice for combating undesired micro-organisms. The compounds are suitable for use as plant protection agent, in particular as fungicides and bactericides.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the compounds, at the concentrations required for combating plant diseases, permits treatment of above-ground parts of plants, of vegetable propagation stock and seeds, and of the soil.

The compounds can be converted to the customary formulations, such as solutions, emulsions, suspensions powders, foams, pastes, granules, aerosols, very fine capsules in polymeric substances and in coating compositions for seed, and ULV-formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as actone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The compounds prepared by the process according to the invention, and their secondary products, can be present in the formulations as a mixture with other known active compounds, such as other fungicides, insecticides and acaricides, and as mixtures with fertilizers and growth regulators.

The compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in a customary manner, for example by watering, spraying, atomizing, scattering, dusting, foaming, painting, etcetera. It is also possible to apply the active compounds by the ultra low volume method, or to inject the formulation of the active compound or the active compound itself into the soil. It is also possible to treat the seed of the plants.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

USE EXAMPLES

In the Use Examples which follow, the compound given here is employed as a comparative substance.

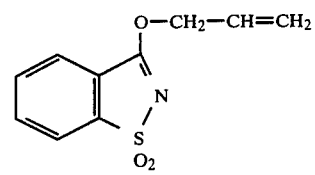

EXAMPLE A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the following example:

TABLE A

| Pyricularia test (rice)/protective | | |
|---|---|---|
| Active compounds | Active compound concentration in % | Disease infestation as a percentage of the untreated control |
| ![structure A (known)] | 0.025 | 25 |
| ![structure with N—NH2 / NH / SO2] | 0.025 | 0 |

EXAMPLE B

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the following examples:

TABLE B

Pyricularia test (rice)/systemic

| Active compounds | Amount applied in mg of active compound per 100 cm² | Disease infestation as a percentage of the untreated control |
|---|---|---|
| (A) (known) O—CH₂—CH=CH₂ structure | 100 | 50 |
| N—NH₂ structure | 100 | 30 |
| N—NH— structure | 100 | 11 |

The compounds which are obtainable by the process according to the invention are, for example, 3-hydrazino-1,2-benzisothiazole 1,1-dioxide, 3-(N,N-dimethylhydrazino)-1,2-benzothiazole 1,1-dioxide, 3-t-butylhydrazino-1,2-benzisothiazole 1,1-dioxide, 3-(N-ethyl-N-methylhydrazino)-1,2-benzisothiazole 1,1-dioxide, 5-chloro-3-hydrazino-1,2-benzisothiazole 1,1-dioxide, 6-chloro-3-hydrazino-1,2-benzisothiazole 1,1-dioxide, 5,6-dichloro-3-hydrazino-1,2-benzisothiazole 1,1-dioxide and 5-chloro-6-methyl-3-hydrazino-1,2-benzisothiazole 1,1-dioxide.

The preparative examples which follow are intended to illustrate the invention in more detail without restricting it.

Preparation Examples

EXAMPLE 1

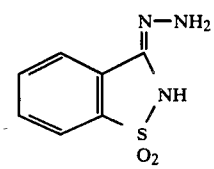

36.6 g (0.2 mol) of 3-keto-2H,3H-1,2-benzisothiazole 1,1-dioxide and 20 g of hydrazine hydrate in 200 ml of n-butanol are boiled under reflux for about 35 hours. The yellow solution is then evaporated down in vacuo, and the residue is stirred with 50 ml of acetic acid. The crystal slurry is filtered under suction, and the crude product which is obtained in this manner and has a melting point of 249° C. can be recrystallized from water. 36.3 g (91% of theory) of 3-hydrazino-2H,3H-1,2-benzisothiazole 1,1-dioxide of melting point 263° C. are obtained.

EXAMPLE 2

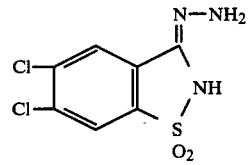

50.2 g (0.2 mol) of 5,6-dichloro-3-keto-2H,3H-1,2-benzisothiazole 1,1-dioxide in 200 ml of diethylene glycol are stirred with 35 g of hydrazine hydrate for 30 hours at 160° C. to 165° C. Working up analogously to Example 1 gives 31.7 g (63% of theory) of 5,6-dichloro-3-hydrazino-1,2-benzisothiazole 1,1-dioxide which decomposes at 276° C.

EXAMPLE 3

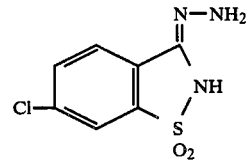

6-Chloro-3-hydrazino-1,2-benzisothiazole 1,1-dioxide is obtained analogously to Example 1, by reacting 6-chloro-3-keto-2H,3H-1,2-benzisothiazole 1,1-dioxide (43.2 g; 0.2 mol) with 35 g of hydrazine hydrate in n-pentanol at 150° C. Yield 33.7 g (78% of theory). M.p.=277° C.

EXAMPLE 4

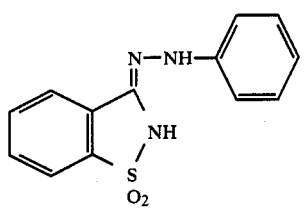

3-Phenyl-hydrazino-1,2-benzisothiazole 1,1-dioxide, which decomposes at 225° C., is obtained analogously to Example 1, in 74% yield, from 3-keto-2H,3H-1,2-benzisothiazole 1,1-dioxide and phenylhydrazine.

EXAMPLE 5

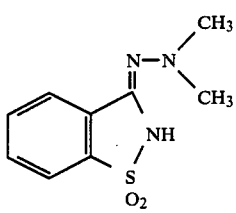

3-(N,N-Dimethylhydrazino)-1,2-benzisothiazole 1,1-dioxide, which decomposes at 238° C., is obtained analogously to Example 1, in 69% yield, from 3-keto-2H,3H-1,2-benzisothiazole 1,1-dioxide and N,N-dimethylhydrazine.

EXAMPLE 6

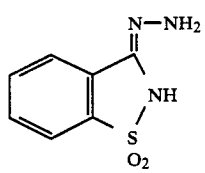

36,6 g (0.2 mol) of 3-keto-2H,3H-1,2-benzisothiazole 1,1-dioxide and 70 g (1,4 mol) of hydrazine hydrate in 250 ml of n-butanol are boiled under reflux for about 25 hours. Further 250 ml n-butanol are added and the solution is then evaporated down in vacuo, and the hemicrystalline residue is stirred with 50 ml of glacial acetic acid. The crystal slurry is filtered under suction. 37,2 g (94% of theory) of 3-hydrazino-2H,3H-1,2-benzisothiazole 1,1-dioxide of melting point 262° C. are obtained.

It will be understood that the specification and examples are illustrative but not limitative of the present invention and that other embodiments within the spirit and scope of the invention will suggest themselves to those skilled in the art.

We claim:

1. A process for the preparation of a 3-hydrazino-1,2-benzisothiazole 1,1-dioxide of the formula

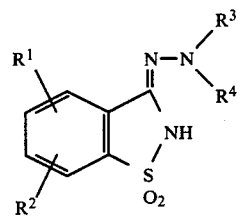

in which
 $R^1$ and $R^2$ each independently is hydrogen, alkyl, halogen, amino, hydroxyl or carboxyl, and
 $R^3$ and $R^4$ each independently is hydrogen, alkyl, cycloalkyl or aryl,
consisting of reacting a 3-keto-2H,3H-1,2-benzisothiazole 1,1-dioxide of the formula

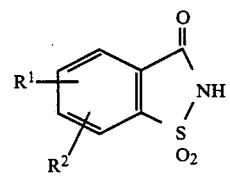

with a hydrazine of the formula

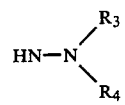

in a molar ratio of 1:1 to 1:50, in an inert solvent, at a temperature between 75° C. and 200° C. and for a reaction time of 15 to 40 hours.

2. A process according to claim 1, wherein the molar ratio is 1:5 to 1:10.

3. A process according to claim 1, wherein the temperature is between 130° C. and 165° C.

4. A process according to claim 1, wherein the solvent is at least one butanol or pentanol.

5. A process according to claim 1, wherein the reaction time is between 30 and 35 hours.

6. A process according to claim 2, wherein the temperature is between 130° C. and 165° C., the solvent is at least one butanol or pentanol and the reaction time is between 30 and 35 hours.

* * * * *